US008870774B2

(12) United States Patent
Kwak et al.

(10) Patent No.: US 8,870,774 B2

(45) Date of Patent: Oct. 28, 2014

(54) ADAPTIVE CLUTTER FILTERING METHOD AND ULTRASOUND SYSTEM FOR THE SAME

(75) Inventors: Han Kwak, Seoul (KR); Jae Keun Lee, Seoul (KR)

(73) Assignee: Samsung Medison Co., Ltd., Hongcheon-Gun, Gangwon-Do (KR)

( * ) Notice: Subject to any disclaimer, the term of this patent is extended or adjusted under 35 U.S.C. 154(b) by 460 days.

(21) Appl. No.: 12/965,499

(22) Filed: Dec. 10, 2010

(65) Prior Publication Data

US 2011/0144489 A1 Jun. 16, 2011

(30) Foreign Application Priority Data

Dec. 14, 2009 (KR) ........................ 10-2009-0123845

(51) Int. Cl.

| | |
|---|---|
| ***A61B 8/00*** | (2006.01) |
| ***G01S 15/89*** | (2006.01) |
| ***A61B 8/08*** | (2006.01) |
| ***G06T 7/00*** | (2006.01) |
| ***G01S 7/52*** | (2006.01) |

(52) U.S. Cl.

CPC ........... *G01S 15/8981* (2013.01); *A61B 8/5207* (2013.01); *A61B 8/488* (2013.01); *A61B 8/0891* (2013.01); *G01S 15/8979* (2013.01); *A61B 8/5215* (2013.01); *A61B 8/00* (2013.01); *G06T 7/0012* (2013.01); *G01S 7/5205* (2013.01)

USPC ............................ 600/441; 600/443; 382/128

(58) Field of Classification Search

None

See application file for complete search history.

(56) References Cited

U.S. PATENT DOCUMENTS

| | | | | |
|---|---|---|---|---|
| 5,524,629 | A | 6/1996 | Mahony | |
| 5,735,797 | A | 4/1998 | Muzilla et al. | |
| 6,406,430 | B1 | 6/2002 | Ishrak et al. | |
| 6,755,787 | B2 * | 6/2004 | Hossack et al. | 600/447 |
| 2003/0097068 | A1 * | 5/2003 | Hossack et al. | 600/443 |
| 2003/0181814 | A1 | 9/2003 | Ji et al. | |
| 2007/0112269 | A1 | 5/2007 | Germond-Rouet et al. | |

FOREIGN PATENT DOCUMENTS

| | | | |
|---|---|---|---|
| EP | 0 947 853 | A2 | 10/1999 |
| JP | 11-347035 | A | 12/1999 |
| JP | 2000-333957 | A | 12/2000 |
| JP | 2005-27942 | A | 2/2005 |
| JP | 2007-507271 | A | 3/2007 |
| KR | 10-2000-0073096 | A | 12/2000 |
| WO | 03/001239 | A2 | 1/2003 |

OTHER PUBLICATIONS

Korean Office Action, issued in Korean Patent Application No. 10-2009-0123845, dated Dec. 28, 2011.

(Continued)

*Primary Examiner* — Long V. Le

*Assistant Examiner* — Amanda Lauritzen Moher

(74) *Attorney, Agent, or Firm* — McDermott Will & Emery LLP

(57) ABSTRACT

There is disclosed an embodiment for adaptive clutter filtering. A signal acquisition unit transmits and receives ultrasound signals to and from a target object to output baseband IQ signals. A memory stores an error condition, a filter decision condition and information on at least two of filters for filtering the baseband IQ signals. A user interface receives a filter selection condition for selecting at least two filters among a plurality of filters stored in the memory. A processor extracts at least two of filters from the memory according to the filter selection condition and the error condition, decides a filter among the extracted at least two of filters and filters the baseband IQ signals by using filter coefficients of the decided filter.

10 Claims, 3 Drawing Sheets

120
100
MEMORY
110
140
150
SIGNAL ACQUISITION UNIT
PROCESSOR
DISPLAY UNIT
USER INTERFACE
130

Stop band
Passband ripple
Passband
Stopband attenuetion
Transition Band
Gain (dB)
Normalized Frequency
10, 0, -10, -20, -30, -40, -50, -60, -70, -80
0, 0.1, 0.2, 0.3, 0.4, 0.5

(56) References Cited

OTHER PUBLICATIONS

Extended European Search Report issued in European Patent Application No. EP 10192788.7 dated Jul. 5, 2013.

Yoo et al., "Adaptive Clutter Rejection for Ultrasound Color Doppler Imaging," Medical Imaging 2005: Ultrasonic Imaging and Signal Processing.

Yoo et al., "Adaptive Clutter Rejection for 3D Color Doppler Imaging: Preliminary Clinical Study," Ultrasound in Med. & Biol., vol. 34, No. 8, pp. 1221-1231, 2008.

Japanese Office Action issued in Japanese Application No. 2010-273767 dated Jul. 29, 2014, w/English translation.

* cited by examiner

FIG. 4

| Ensemble \ Cutoff | 0.05 (Pif) | 0.06 | 0.07 | 0.08 | 0.09 | ... | 0.20 | 0.21 | 0.22 | 0.23 | ... |
|---|---|---|---|---|---|---|---|---|---|---|---|
| 1 | | | | | | | | | | | |
| 2 | Filter_A | Filter_A | Filter_C | Filter_C | Filter_C | ... | Filter_D | Filter_D | Filter_B | Filter_A | ... |
| 3 | Filter_A | Filter_B | Filter_C | Filter_B | Filter_C | ... | Filter_B | Filter_B | Filter_B | Filter_D | ... |
| 4 | Filter_A | Filter_C | Filter_B | Filter_C | Filter_D | ... | Filter_B | Filter_D | Filter_C | Filter_A | ... |
| ... | ... | ... | ... | ... | ... | ... | ... | ... | ... | ... | ... |
| 11 | Filter_D | Filter_C | Filter_C | Filter_D | Filter_D | ... | Filter_D | Filter_D | Filter_D | Filter_D | ... |
| 12 | Filter_C | Filter_C | Filter_A | Filter_D | Filter_D | ... | Filter_D | Filter_D | Filter_B | Filter_D | ... |
| 13 | Filter_D | Filter_C | Filter_D | Filter_D | Filter_B | ... | Filter_D | Filter_D | Filter_D | Filter_B | ... |
| 14 | Filter_C | Filter_A | Filter_D | Filter_D | Filter_D | ... | Filter_D | Filter_D | Filter_B | Filter_D | ... |
| 15 | Filter_C | Filter_D | Filter_D | Filter_B | Filter_D | ... | Filter_D | Filter_B | Filter_D | Filter_D | ... |
| ... | ... | ... | ... | ... | ... | ... | ... | ... | ... | ... | ... |

ADAPTIVE CLUTTER FILTERING METHOD AND ULTRASOUND SYSTEM FOR THE SAME

CROSS-REFERENCE TO RELATED APPLICATIONS

The present application claims priority from Korean Patent Application No. 10-2009-0123845 filed on Dec. 14, 2009, the entire subject matter of which is incorporated herein by reference.

TECHNICAL FIELD

The present invention generally relates to ultrasound systems, and more particularly to an ultrasound system and method for adaptive clutter filtering.

BACKGROUND

An ultrasound system has become an important and popular diagnostic tool due to its non-invasive and non-destructive nature. The ultrasound system can provide high dimensional real-time ultrasound images of inner parts of target objects without a surgical operation. The ultrasound system may operate in various image modes such as a brightness mode, a Doppler mode and the like to acquire the ultrasound images for diagnosis.

In the Doppler mode, the ultrasound system can provide a color Doppler mode image that visualizes velocities of moving objects (e.g., blood flow, heart, etc.) or scattered objects. The color Doppler mode image includes a power mode image visualizing powers of Doppler signals as two-dimensional (2D) distribution and a velocity mode image visualizing velocities of the moving objects, which may be computed from the Doppler signals, as 2D distribution. The color Doppler mode image not only visualizes the blood flow in real time but also represents a status of the blood flow at a wide range from the blood flow of a high velocity in a large vessel to the blood flow of a low velocity in a small vessel.

The Doppler signals may include low frequency signals (so-called clutter signals) due to motion of a cardiac wall or valve of a heart. The clutter signals can be an obstacle to accurately detecting velocities of the blood flow. Thus, the ultrasound system may employ a clutter filter to remove the clutter signals.

The clutter signals are typically distributed at the low frequency band and pure Doppler signals are typically distributed at a high frequency band. Thus, a high pass filter may be used to extract the pure Doppler signals. Since the clutter signals have higher amplitude than the Doppler signals, it is required to use a high pass filter of good performance to extract the pure Doppler signals.

SUMMARY

An embodiment for adaptive clutter filtering is disclosed herein. In one embodiment, by way of non-limiting example, an ultrasound system may include: a signal acquisition unit configured to transmit and receive ultrasound signals to and from a target object to output baseband In-phase Quadtrature (IQ) signals; a memory configured to store an error condition, a filter decision condition and information on at least two filters for filtering the baseband IQ signals; a user interface configured to receive a filter selection condition for selecting at least two filters among a plurality of filters stored in the memory; and a processor configured to extract at least two filters from the memory according to the filter selection condition and the error condition, decide a filter among the extracted at least two filters and filter the baseband IQ signals by using filter coefficients of the decided filter.

In another embodiment, a method of implementing adaptive clutter filtering may comprise: transmitting and receiving ultrasound signals to and from a target object to output baseband IQ signals; receiving a filter selection condition for selecting at least two filters among a plurality of filters stored in a memory, wherein the memory comprises the filter selection condition, an error condition and a filter decision condition; extracting at least two filters from the memory according to the filter selection condition and the error condition; deciding a filter among the extracted at least two filters based on the filter decision condition; and filtering the baseband IQ signals by using filter coefficients of the decided filter.

This Summary is provided to introduce a selection of concepts in a simplified form that are further described below in the Detailed Description. This Summary is not intended to identify key or essential features of the claimed subject matter, nor is it intended to be used in determining the scope of the claimed subject matter.

BRIEF DESCRIPTION OF THE DRAWINGS

FIG. 4 is a schematic diagram showing an example of a filter table.

DETAILED DESCRIPTION

This detailed description is provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
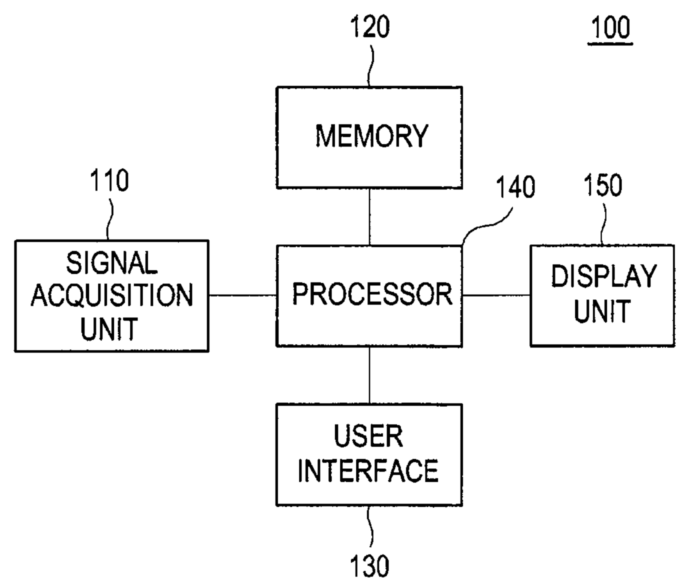
FIG. 1 is a block diagram showing an illustrative embodiment of an ultrasound system.

FIG. 1 is a block diagram showing an illustrative embodiment of an ultrasound system. As depicted therein, the ultrasound system 100 may include a signal acquisition unit 110, a memory 120, a user interface 130, a processor 140 and a display unit 150.

The signal acquisition unit 110 may be configured to transmit and receive ultrasound signals to and from a target object to thereby output baseband IQ signals to be used in forming frames. The frames may include color Doppler mode image frames.

Figure 2:
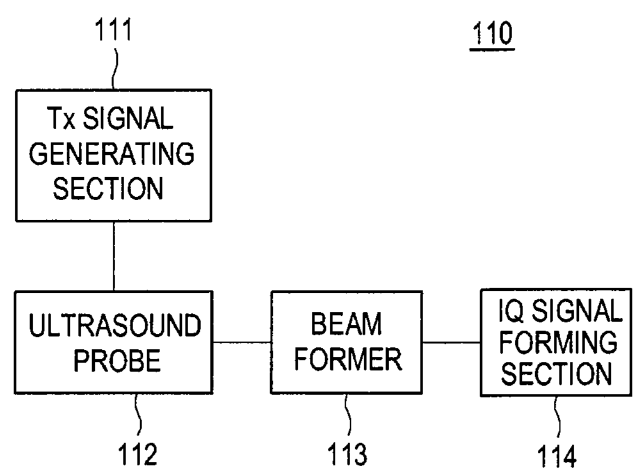
FIG. 2 is a block diagram showing an illustrative embodiment of a signal acquisition unit in FIG. 1.

FIG. 2 is a block diagram showing an illustrative embodiment of the signal acquisition unit 110. The signal acquisition unit 110 may include a transmit (Tx) signal generating section 111, an ultrasound probe 112 having a plurality of transducer elements (not shown), a beam former 113 and a IQ signal forming section 114.

The Tx signal generating section 111 may be configured to generate Tx signals. The Tx signal generating section 111 may generate the Tx signals and apply delays to the Tx signals in consideration of distances between the respective transducer elements and focal points for acquiring ultrasound images indicative of the target object. The ultrasound images may include the color Doppler mode image.

The ultrasound probe 112 may include the plurality of transducer elements for reciprocally converting between electrical signals and ultrasound signals. The ultrasound probe 112 may transmit ultrasound signals to the target object in response to the Tx signals provided from the Tx signal generating section 111. The ultrasound probe 112 may receive ultrasound echo signals reflected from the target object to thereby output the received signals. The transmission and reception of the ultrasound signals may be sequentially and iteratively carried out to form the received signals. The received signals may be analog signals. The ultrasound probe 112 may include a three-dimensional mechanical probe, a 2D array probe and the like. However, it should be noted herein that the ultrasound probe 112 may not be limited thereto.

The beam former 113 may convert the received signals provided from the ultrasound probe 112 into digital signals. The beam former 113 may apply delays to the digital signals in consideration of distances between the transducer elements and focal points to thereby output digital receive-focused signals.

The IQ signal forming section 114 may perform decimation on the digital receive-focused signals to thereby form the baseband IQ signal. The baseband IQ signal may include clutter signals due to reflection of the ultrasound signals from stationary or slowly moving tissues, Doppler signals due to the reflection of the ultrasound signals from blood flow, and noise signals. The decimation is a technique for reducing the number of samples of the baseband IQ signal.

Referring back to FIG. 1, the memory 120 may store a plurality of filter coefficients of a plurality of filters for clutter filtering. The filter coefficients may be determined and stored according to various storage conditions such as filter types, filter orders, ensemble numbers, cutoff frequencies, stopband attenuations, stopband widths, passband gains, passband ripples and the like. The ensemble numbers may represent the number of transmission and reception of the ultrasound signals for acquiring the Doppler signals of a scanline.

Figure 3:
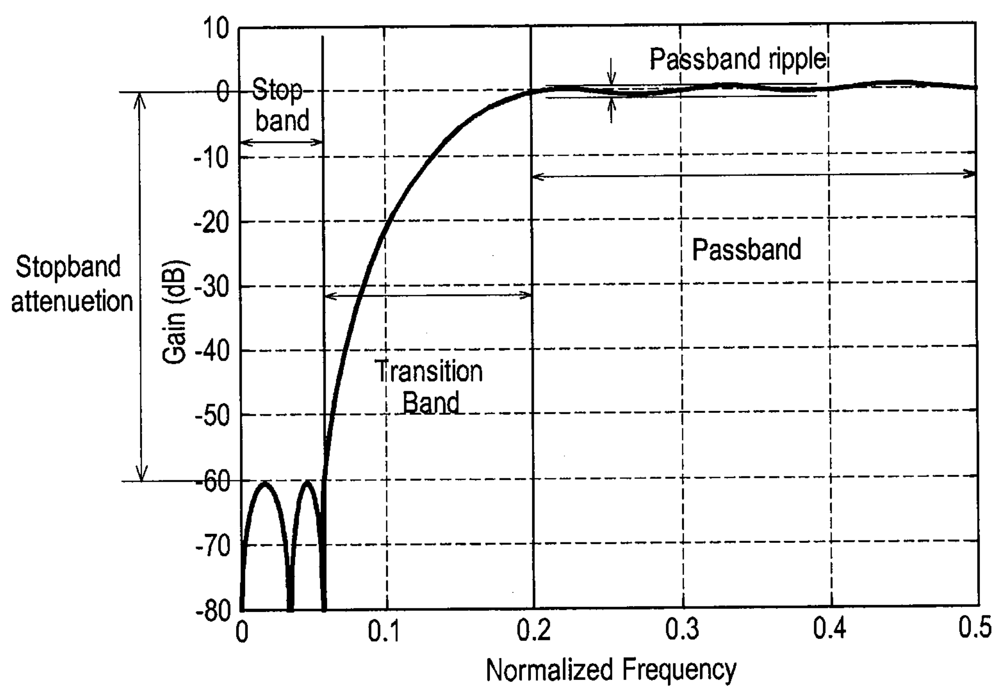
FIG. 3 is a graph showing an example of a response curve of a high pass filter.

FIG. 3 is a graph showing an example of a response curve of a high pass filter. The graph may show a stopband to be removed after the clutter filtering, a passband to be remained after the clutter filtering, a transition band between the stopband and the passband, a stopband attenuation indicative of a gain of the stopband and a passband ripple. The filter may include a finite impulse response (FIR) filter, an infinite impulse response (IIR) filter, and a regression filter and the like. In the case of using the IIR filter, various initialization techniques may be used to remove a transient state. The initialization techniques may include zero, step, exponential, and projection initialization techniques and the like. The regression filter may be classified into a polynomial regression filter, a sinusoidal regression filter and the like according to a basis function thereof.

FIG. 4 is a schematic diagram showing an example of a filter table, which shows filters determined according to the ensemble number and the cutoff frequency at a stopband of 60 dB. In the filter table shown in FIG. 4, Filter_A may be one of a 1st order projection-initialized IIR Butterworth filter to a 10th order projection-initialized IIR Butterworth filter, Filter B may be one of a 1st order projection-initialized IIR Elliptic filter to a 10th order projection-initialized IIR Butterworth filter, Filter_C may be a modified polynomial regression filter, and the Filter_D may be a modified sinusoidal regression filter. But, the filter types may not be limited thereto. In one embodiment, it may be possible to add a new filter to the filter table or delete a filter from the filter table.

The memory 120 may store information on an error condition for determining filters that are matched corresponding to a filter selection condition. The error condition may be indicative of a specific filter property and inputted through the user interface 130 when extracting filters from the filter table. In one embodiment, the error condition may include a permissible matching range, e.g., +/−10% with respect to the filter selection condition.

Furthermore, the memory 120 may store information on filter decision condition for deciding one of the filters selected according to the filter selection condition and the error condition. In one embodiment, the filter decision condition may include a condition for selecting a filter having the widest stopband, a condition for selecting a filter having the narrowest transitionband, a condition for selecting a filter having the best phase response and the like.

The user interface 130 may receive the filter selection condition for selecting at least two filters among a plurality of filters stored in the memory 120. The filter selection condition may be a condition for selecting whole or partial filter coefficients stored in the memory 120. The filter selection condition may be defined by specifying the ensemble number, the cutoff frequency, the stopband attenuation, the filter order, the passband ripple and the like. In one embodiment, the ensemble number may be in a range of 2-32, the cutoff frequency may be ranging from 0.05 Hz to 0.44 Hz, the stopband attenuation may be ranging from 40 dB to 100 dB, and the filter order may be in a range of 1-10.

The processor 140 may extract filters from the filter table stored in the memory 120 by using the filter selection condition and the error condition and decide a proper filter among the extracted filters by using the filter decision condition. The processor 140 may filter the baseband IQ signals by using the filter coefficients of the decided filter to thereby extract the Doppler signals from the baseband IQ signals. The processor 140 may form the color Doppler mode image by using the extracted Doppler signals. The color Doppler mode image includes a power mode image that visualizes powers of Doppler signals as two-dimensional (2D) distribution and a velocity mode image that visualizes velocities of the moving objects, whose velocities may be computed from the Doppler signals, as 2D distribution. Because the clutter signal included in the baseband IQ signal is mostly spread through low frequency band while the Doppler signal is spread through high frequency band, the processor 140 may filter the baseband IQ signal by using a high pass filter to extract the Doppler signal.

The display unit 150 may display the color Doppler mode image formed by the processor 140. The display unit 150 may include a cathode ray tube (CRT) display, a liquid crystal display (LCD), an organic light emitting diodes (OLED) display and the like.

Any reference in this specification to "one embodiment," "an embodiment," "example embodiment," "illustrative embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to affect such feature, structure or characteristic in connection with other embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:

a signal acquisition device, including at least an ultrasound probe, configured to transmit and receive ultrasound signals to and from a target object to output baseband In-phase Quadrature (IQ) signals;

a memory configured to store a filter table, an error condition, a filter decision condition and information on a plurality of filters for filtering the baseband IQ signals;

a user interface unit, connected to the memory, configured to receive a filter selection condition for selecting at least two filters among the plurality of filters stored in the memory; and a processor, connected to the memory, configured to extract at least two filters from the filter table according to the filter selection condition and the error condition, select a filter among the extracted at least two filters and filter the baseband IQ signals by using filter coefficients of the selected filter.

2. The ultrasound system of claim 1, wherein the signal acquisition device comprises:

a transmit (Tx) signal generator connected to the ultrasound probe and configured to generate Tx signals, wherein the ultrasound probe is configured to transmit ultrasound signals to the target object in response to the Tx signals and receive ultrasound echo signals reflected from the target object to output the received signals;

a beam former, connected to the ultrasound probe, configured to convert the received signals into digital signals and apply delays to the digital signals in consideration of distances between transducer elements and focal points to output digital receive-focused signals; and an IQ signal former, connected to the ultrasound probe, configured to perform decimation on the digital receive-focused signals to form the baseband IQ signal.

3. The ultrasound system of claim 1, wherein the filter selection condition is defined by at least one of an ensemble number, a cutoff frequency, a stopband attenuation, a filter order and a passband ripple.

4. The ultrasound system of claim 1, wherein the error condition includes a permissible matching range with respect to the filter selection condition.

5. The ultrasound system of claim 1, wherein the filter decision condition includes one of a condition for selecting a filter having a widest stopband, a condition for selecting a filter having a narrowest transitionband and a condition for selecting a filter having a desired phase response, with respect to each other.

6. An adaptive clutter filtering method in an ultrasound system including a signal acquisition device comprising at least an ultrasound probe, a memory, a user interface unit connected to the memory, and a processor connected to the memory, the method comprising:

transmitting and receiving, by the signal acquisition device, ultrasound signals to and from a target object to output baseband In-phase Quadrature (IQ) signals;

receiving, by the user interface unit, a filter selection condition for selecting at least two filters among a plurality of filters stored in the memory, wherein the memory stores the filter selection condition, an error condition and a filter decision condition;

extracting, by the processor, at least two filters from a filter table according to the filter selection condition and the error condition;

selecting, by the processor, a filter among the extracted at least two filters based on the filter decision condition; and filtering, by the processor, the baseband IQ signals by using filter coefficients of the selected filter.

7. The method of claim 6, wherein the transmitting and receiving ultrasound signals comprises:

generating, by the signal acquisition device, transmit (Tx) signals;

transmitting, by the signal acquisition device, ultrasound signals to the target object in response to the Tx signals and receiving ultrasound echo signals reflected from the target object to output the received signals;

converting, by the signal acquisition device, the received signals into digital signals and applying delays to the digital signals in consideration of distances between transducer elements and focal points to output digital receive-focused signals; and performing, by the signal acquisition device, decimation on the digital receive-focused signals to form the baseband IQ signal.

8. The method of claim 6, wherein the filter selection condition is defined by at least one of an ensemble number, a cutoff frequency, a stopband attenuation, a filter order and a passband ripple.

9. The method of claim 6, wherein the error condition includes a permissible matching range with respect to the filter selection condition.

10. The method of claim 6, wherein the filter decision condition includes one of a condition for selecting a filter having a widest stopband, a condition for selecting a filter having a narrowest transitionband and a condition for selecting a filter having a desired phase response, with respect to each other.

* * * * *